United States Patent [19]

Lang et al.

[11] Patent Number: 5,665,739
[45] Date of Patent: Sep. 9, 1997

[54] SUBSTITUTED BENZOYLGUANIDINES, PROCESS AND THEIR PREPARATION, THEIR USE AS PHARMACEUTICAL OR DIAGNOSTIC, AND PHARMACEUTICAL CONTAINING THEM

[75] Inventors: Hans-Jochen Lang, Hofheim/Taunus; Heinz-Werner Kleeman, Bad Homburg; Wolfgang Scholz, Eschborn; Udo Albus, Florstadt, all of Germany

[73] Assignee: Hoechst Aktiengesellschaft, Frankfurt am Main, Germany

[21] Appl. No.: 440,619

[22] Filed: May 15, 1995

Related U.S. Application Data

[63] Continuation-in-part of Ser. No. 334,008, Nov. 2, 1994, abandoned, which is a continuation of Ser. No. 165,649, Dec. 13, 1993, abandoned.

[30] Foreign Application Priority Data

Dec. 15, 1992 [DE] Germany .............. 42 42 191.8
Apr. 9, 1993 [DE] Germany .............. 43 11 800.3

[51] Int. Cl.⁶ .............. A61K 31/44; C07D 213/02
[52] U.S. Cl. .............. 514/345; 514/307; 514/311; 514/346; 514/351; 514/383; 514/399; 514/427; 546/290; 546/291; 546/152; 546/139; 548/267.4; 548/343.5; 548/563
[58] Field of Search .............. 546/290, 291, 546/139, 152; 514/345, 346, 357, 311, 307, 383, 399, 427; 548/563, 267.4, 343.5

[56] References Cited

U.S. PATENT DOCUMENTS

| | | | |
|---|---|---|---|
| 3,780,027 | 12/1973 | Cragoe, Jr. et al. | 549/494 |
| 5,091,394 | 2/1992 | Englert et al. | 514/331 |
| 5,373,024 | 12/1994 | Lang et al. | 514/618 |

Primary Examiner—Shailendra Kumar
Attorney, Agent, or Firm—Finnegan, Henderson, Farabow, Garrett & Dunner, L.L.P.

[57] ABSTRACT

Benzoylguanidines of the formula I are described

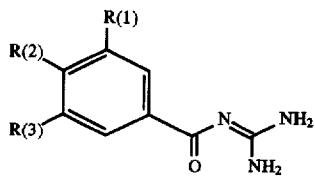

in which

R(1)=hydrogen, Hal, —NO$_2$, —C≡N, —CF$_3$, R(4)—SO$_m$ or R(5)R(6)N—SO$_2$—, R(4) and R(5) are alk(en)yl or CF$_3$, R(5) also having the meaning of H, R(2)=is heteroaryl or —SR(10), —OR(10), —NR(10)R(11), —CR(10)R(11)R(12); where R(10) is —C$_a$H$_{2a}$-heteroaryl, and R(11) and R(12) are as defined for R(10) and also hydrogen or alkyl, R(3) is as defined for R(1) or is alkyl, —X—R(13) where X is oxygen, S, NR(14), where R(13) is H or (cyclo)alkyl.

They are obtained from a compound of the formula II

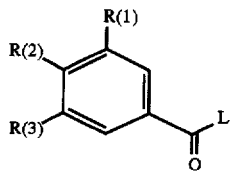

by reacting it with guanidine. The compounds are outstandingly suitable as antiarrhythmic pharmaceuticals with a cardioprotective component for the prophylaxis and treatment of infarctions and for the treatment of angine pectoris, and they also preventively inhibit, or greatly reduce, the pathophysiological processes in the formation of ischemia-induced damage, in particular in the triggering of ischemia-induced cardiac arrhythmias.

11 Claims, No Drawings

SUBSTITUTED BENZOYLGUANIDINES, PROCESS AND THEIR PREPARATION, THEIR USE AS PHARMACEUTICAL OR DIAGNOSTIC, AND PHARMACEUTICAL CONTAINING THEM

This application is a continuation-in-part of U.S. patent application Ser. No. 08/334,008 filed Nov. 2, 1994 now abandoned, which is a continuation of U.S. patent application Ser. No. 08/165,649 filed Dec. 13, 1993 now abandoned. Both applications are incorporated by reference herein in their entirety.

The invention relates to benzoylguanidines of the formula I

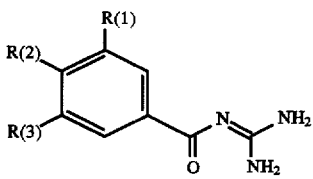

in which

R(1) is hydrogen, F, Cl, Br, I, —NO$_2$, —C≡N, R(16)-C$_p$H$_{2p}$—O$_q$, R(4)-SO$_m$ or R(5)R(6)N—SO$_2$—;
p is zero, 1, 2 or 3;
q is zero or 1;
R(16) is C$_r$F$_{2r+1}$;
r is 1, 2 or 3,
m is zero, 1 or 2;
R(4) and R(5) independently of one another are (C$_1$-C$_8$)-alkyl, (C$_3$-C$_6$)-alkenyl, —C$_n$H$_{2n}$—R(7) or CF$_3$;
n is zero, 1, 2, 3 or 4
R(7) is (C$_3$-C$_7$)-cycloalkyl or phenyl, which is unsubstituted or substituted by 1-3 substituents selected from the group consisting of F, Cl, CF$_3$, methyl, methoxy and NR(8)R(9);
R(8) and R(9) are H or C$_1$-C$_4$-alkyl; or
R(5) is H;
R(6) H or (C$_1$-C$_4$)-alkyl; or
R(5) and R(6) are together 4 or 5 methylene groups, of which one CH$_2$ group can be replaced by oxygen, S, NH, N—CH$_3$ or N-benzyl;
R(2) is (C$_1$-C$_9$)-heteroaryl, which is linked via C or N and which is unsubstituted or substituted by 1-3 substituents selected from the group consisting of F, Cl, CF$_3$, CH$_3$, methoxy, hydroxy, amino, methylamino and dimethylamino; or
R(2) is —SR(10), —OR(10), —NR(10)R(11) or —CR(10)R(11)R(12);
R(10) is —C$_a$H$_{2a}$—(C$_1$-C$_9$)-heteroaryl, which is unsubstituted or substituted by 1-3 substituents selected from the group consisting of F, Cl, CF$_3$, CH$_3$, methoxy, hydroxyl, amino, methylamino and dimethylamino;
a zero, 1 or 2;
R(11) and R(12) independently of one another have the definition given for R(10) or are hydrogen or (C$_1$-C$_4$)-alkyl;
R(3) has the definition given for R(1) or is (C$_1$-C$_6$)-alkyl or —X—R(13);
X is oxygen, S or NR(14);
R(14) is H or (C$_1$-C$_3$)-alkyl;
R(13) is H, (C$_1$-C$_6$)-alkyl, (C$_3$-C$_8$)-cycloalkyl or —C$_b$H$_{2b}$—R(15);
b is zero, 1, 2, 3 or 4;
R(15) is phenyl which is unsubstituted or substituted by 1-3 substituents selected from the group consisting of F, Cl, CF$_3$, methyl, methoxy and NR(8)R(9);
R(8) and R(9) H or (C$_1$-C$_4$)-alkyl;
with the exception of compounds I in which R(1) is R(4)-SO$_m$ or R(5)NSO$_2$ and R(2) simultaneously is (C$_1$-C$_9$)-heteroaryl,
and the pharmaceutically acceptable salts thereof.

Preferred compounds of the formula I are those in which:
R(1) is hydrogen, F, Cl, —C≡N, R(16)-C$_p$H$_{2p}$—O$_q$, R(4)-SO$_m$ or R(5)R(6)N—SO$_2$—;
p is zero, 1, 2 or 3;
q is zero or 1;
R(16) is C$_r$F$_{2r+1}$;
r is 1, 2 or 3;
m is zero, 1 or 2;
R(4) and R(5) independently of one another are (C$_1$-C$_8$)-alkyl, (C$_3$-C$_4$)-alkenyl, —C$_n$H$_{2n}$—R(7) or —CF$_3$;
n is zero or 1;
R(7) is (C$_3$-C$_6$)-cycloalkyl or phenyl, which is unsubstituted or substituted by 1-3 substituents selected from the group consisting of F, Cl, CF$_3$, methyl, methoxy and NR(8)R(9);
R(8) and R(9) independently of one another are H or methyl; or
R(5) is H;
R(6) is H or methyl;
R(3) is hydrogen, methyl, cyano, —CF$_3$, F or Cl, with the exception of compounds I in which R(1) is R(4)-SO$_m$ or R(5)NSO$_2$ and
R(2) simultaneously is (C$_1$-C$_9$)-heteroaryl,
and the pharmaceutically acceptable salts thereof.

Particularly preferred compounds I are those in which:
R(1) is hydrogen, F, Cl, —C≡N, —CF$_3$, R(4)—SO$_m$ or R(5)R(6)N—SO$_2$;
m is zero, 1 or 2;
R(4) is methyl or CF$_3$;
R(5) and R(6) independently of one another are H or methyl;
R(2) is (C$_1$-C$_9$)-heteroaryl, which is linked via C or N and which is unsubstituted or substituted by a radical selected from the group consisting of F, Cl, CF$_3$, CH$_3$, methoxy arid dimethylamino; or
R(2) is —SR(10), —OR(10), —NR(10)R(11) or —CR(10)R(11)R(12);
R(10) is —C$_a$H$_{2a}$—(C$_1$-C$_9$)-heteroaryl, which is unsubstituted or substituted by a radical selected from the series consisting of F, Cl, CF$_3$, CH$_3$, methoxy and dimethylamino;
a is zero, 1 or 2;
R(11) and R(12) independently of one another are hydrogen or methyl;
R(3) is methyl, cyano, trifluoromethyl, F, Cl or hydrogen;
with the exception of compounds I in which R(1) is R(4)-SO$_m$ or R(5)NSO$_2$ and R(2) simultaneously is (C$_1$-C$_9$)-heteroaryl,
and pharmaceutically acceptable salts thereof.

(C$_1$-C$_9$)-Heteroaryl is to be understood as meaning, in particular, radicals which are derived from phenyl or naphthyl and in which one or more CH groups are replaced by N and/or in which at least two adjacent CH groups (while forming a five-membered aromatic ring) are replaced by S, NH or O. Moreover, it is also possible for one or both atoms of the condensation site of bicyclic radicals (as in indolizinyl) to be N atoms.

Heteroaryl means, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl.

Preferred are pyrrolyl, imidazolyl, triazolyl, pyridyl, quinolyl and isoquinolyl.

If one of the substituents R(1) to R(3) contains one or more asymmetric centers, they can have either the S or the R configuration. The compounds can exist as optical isomers, diastereomers, racemates or mixtures of these.

The alkyl radicals which have been mentioned can be straight-chain or branched.

The invention furthermore relates to a process for the preparation of the compound I, which comprises reacting compounds of the formula II

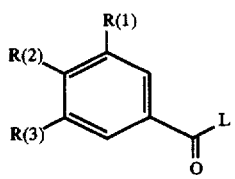

with guanidine, R(1) to R(3) having the abovementioned meaning and L being a leaving group which can readily be substituted by a nucleophile.

The activated acid derivatives of the formula II, in which L is an alkoxy group, preferably a methoxy group, a phenoxy group, a phenylthio, methylthio or 2-pyridylthio group, or a nitrogen heterocycle, preferably 1-imidazolyl, are obtained advantageously in a manner known per se from the carbonyl chlorides (formula II, L=Cl) on which they are based and which, in turn, can be prepared in a manner known per se from the carboxylic acids (formula II, L=OH) on which they are based, for example thionyl chloride.

In addition to the carbonyl chlorides of the formula II (L=Cl), other activated acid derivatives of the formula II can also be prepared, in a manner known per se, directly from the benzoic acid derivatives (formula II, L=OH) on which they are based, for example the methyl esters of the formula II where L=OCH$_3$ by treatment with gaseous HCl in methanol, the imidazolides of the formula II by treatment with carbonyl diimidazole [L=imidazolyl, Staab, Angew. Chem. Int. Ed. Engl. 1,351-367 (1962)], the mixed anhydrides II with Cl—COOC$_2$H$_5$ or tosyl chloride in the presence of triethylamine in an inert solvent, and benzoic acids can be activated with dicyclohexylcarbodiimide (DCC)or with O-[(cyano(ethoxycarbonyl)methylene)amino]-1,1,3,3-tetramethyluronium tetrafluoroborate ("TOTU") [Proceedings of the 21$^{st}$ European Peptide Symposium, Peptides 1990, Editors E. Giralt and D. Andreu, Escom, Leiden, 1991]. A series of suitable methods for the preparation of activated carboxylic acid derivatives of the formula II can be found in J. March, Advanced Organic Chemistry, Third Edition (John Wiley & Sons, 1985), p. 350, where the references are cited.

An activated carboxylic acid derivative of the formula I is reacted with guanidine in a manner known per se in a protic or aprotic polar, but inert, organic solvent. Methanol, isopropanol or THF have proven themselves in the reaction of the methyl benzoates (II, L=OMe) with guanidine, the temperatures being 20° C. to the boiling point of these solvents. In most reactions of compounds II with salt-free guanidine, the process was advantageously carried out in aprotic inert solvents, such as THF, dimethoxyethane or dioxane. Even so, water together with a base such as NaOH, can be used as solvent in the reaction of II and III.

If L=Cl, the process is carried out advantageously with an addition of an acid scavenger, for example in the form of excess guanidine, to bind the hydrohalic acid.

Some of the basic benzoic acid derivatives of the formula II are known and described in the literature. The unknown compounds of the formula II can be prepared by methods known from the literature, for example by converting 4-(or 5-)halo-3-chlorosulfonylbenzoic acids with ammonia or amines into 3-aminosulfonyl-4-(or -5-)halobenzoic acids, or by converting 4-(or 5-)halo-3-chlorosulfonylbenzoic acids with a mild reducing agent, such as sodium bisulfite and subsequently alkylating the product to give 3-alkylsulfonyl-4-(or ° 5-)halobenzoic acids, and reacting the benzoic acids obtained by one of the above-described process variants to give compounds I according to the invention.

Some substituents can successfully be introduced into the 4- and 5-position by methods which are known from the literature, namely palladium-mediated cross coupling of aryl halides with, for example, organostannanes, organoboric acids or organoboranes, or organocopper or organozinc compounds.

In general, benzoylguanidines are weak bases and can bind acid with the formation of salts. Suitable acid addition salts are salts of all pharmacologically acceptable acids, for example halides, in particular hydrochlorides, lactates, sulfates, citrates, tartrates, acetates, phosphates, methylsulfonates and p-toluenesulfonates.

The compounds I are substituted acylguanidines. The best-known representative of the acylguanidines is the pyrazine derivative amiloride, which is used in therapy as a potassium-retaining diuretic. A large number of other amiloride-type compounds are described in the literature, for example diemthylamiloride or ethylisopropylamiloride.

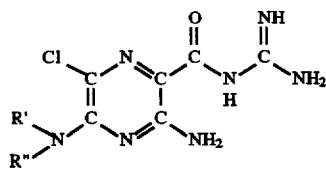

Amiloride: R', R"=H
Dimethylamiloride: R', R"=CH$_3$
Ethylisopropylamiloride: R'=C$_2$H$_5$, R"=CH(CH$_3$)$_2$ Moreover, tests are known which suggest that amiloride has antiarrhythmic properties (Circulation 79, 1257-63 (1989). However, its broad use as an antiarrhythmic is restricted by the fact that this effect is only weakly pronounced and accompanied by a hypotensive and saluretic activity, and these side effects are undesired in the treatment of cardiac arrhythmias.

Experiments on isolated animal hearts have also suggested that amiloride has antiarrhythmic properties (Eur. Heart J. 9 (suppl. 1): 167 (1988) (book of abstracts). For example, it has been found on rats' hearts that artificially induced ventricular fibrillation can be suppressed completely by amiloride. In this model, the abovementioned amiloride derivative ethylisopropylamiloride was even more potent than amiloride itself.

U.S. Pat. No. 5,091,394 (HOE 89/F 288) describes benzoylguanidines which have a hydrogen atom in the position which corresponds to the radical R(1). U.S. patent application Ser. No. 15 926, now U.S. Pat. No. 5,373,024 [German Patent Applications P 42 04 575.4 (HOE 92/F 034)]proposes 3,5-substituted benzoylguanidines in which, however, the substituents R(2) and R(3) do not have the meanings claimed in the present invention.

U.S. Pat. No. 3,780,027 claims acylguanidines whose structure is similar to those of the compounds I and which are derived from commercially available loop diuretics, such as bumetanide. Accordingly, a powerful saluretic activity is reported of these compounds.

It was therefore surprising that the compounds according to the invention have no undesired, disadvantageous saluretic properties, but have a very good activity against arrhythmias as they occur, for example, in connection with oxygen deficiencies. Due to their pharmacological properties, the compounds are highly suitable for use as antiarrhythmics with a cardioprotective component for the prophylaxis and treatment of cardiac infarctions and for the treatment of angina pectoris, in which context they also preventively inhibit, or reduce greatly, the pathophysiological processes in the formation of ischemia-induced damage, in particular when ischemia-induced cardiac arrhythmias are triggered. Due to inhibition of the cellular $Na^+/H^+$ exchange mechanism, the compounds of the formula I according to the invention, which have a protective activity against pathological hypoxic and ischemic situations, can be used as pharmaceuticals for the treatment of all acute or chronic damage triggered by ischemia or for the treatment of directly or collaterally induced diseases. This applies to their use as pharmaceuticals for surgical intervention, for example in connection with organ transplants, where the compounds can be used for the protection of the organs in the donor before and during their removal, for the protection of removed organs, for example in their treatment with, or storage in, physiological baths, and for the transfer into the recipient organism. Equally, the compounds are valuable protective pharmaceuticals when angioplastic curative interventions are carried out, for example on the heart or on peripheral blood vessels. Due to their protective activity against ischemia-induced damage, the compounds are also suitable as pharmaceuticals for the treatment of ischemias of the nervous system, in particular, the central nervous system, where they are suitable, for example, for the treatment of apoplexes and brain edemas. Moreover, the compounds of the formula I according to the invention are also suitable for the treatment of forms of shock, for example allergic, cardiogenic, hypovolemic and bacterial shock.

Moreover, the compounds of the formula I according to the invention are distinguished by powerful inhibitory action on cell proliferations, for example fibroblast proliferation and proliferation of the smooth vascular muscle cells. This is why the compounds of the formula I are suitable as valuable therapeutic agents for diseases in which cell proliferation is a primary or secondary cause, and they can therefore be used as antiatherosclerotics, agents against diabetic late complications, cancers, fibrotic disorders, such as pulmonary fibrosis, hepatic fibrosis or renal fibrosis, organ hypertrophias and hyperplasias, in particular in prostatic hyperplasia or prostatic hypertrophia.

The compounds according to the invention are valuable inhibitors of the cellular sodium proton antiporter ($Na^+/H^+$ exchanger), which is elevated in a large number of diseases (essential hypertension, atherosclerosis, diabetes and the like) even in those cells which are readily accessible to measurements, such as in erythrocytes, thrombocytes or leukocytes. The compounds according to the invention are therefore suitable as outstanding and simple scientific tools, for example in their use as diagnostics for determining, and distinguishing between, certain forms of hypertension, but also of atherosclerosis, diabetes, proliferative disorders and the like. Moreover, the compounds of the formula I are suitable for preventive therapy for preventing the genesis of hypertension, such as of essential hypertension.

In contrast to the known compounds, the solubility in water of the compounds according to the invention is significantly improved. They are therefore much better suited to intravenous administration.

Pharmaceuticals which contain a compound I can be administered orally, parenterally, intravenously, rectally or by inhaling, the preferred way of administration depending on the particular symptom of the disease. The compounds I can be used by themselves or together with galenic auxiliaries, and they can be employed both in veterinary medicine and human medicine.

A person skilled in the art knows, on the basis of his expert knowledge, which auxiliaries are suitable for the desired pharmaceutical formulation. Auxiliaries which can be used in addition to solvents, gel formers, bases for suppositories, tableting auxiliaries, and other excipients for active substances are, for example, antioxidants, dispersants, emulsifiers, antifoams, flavor improvers, preservatives, solubilizers or colorants.

For an oral dosage form, the active compounds together with the suitable additives, such as carriers, stabilizers or inert diluents, are mixed and formulated by customary methods to give suitable dosage forms, such as tablets, sugar-coated tablets, hard gelatin capsules, or aqueous, alcoholic or oily solutions. Inert excipients which can be used are, for example, gum arabic, magnesia, magnesium carbonate, potassium phosphate, lactose, glucose or starch, in particular maize starch. Dry granules or moist granules can be used for the preparation. Examples of oily excipients or examples of solvents are vegetable or animal oils, such as sunflower oil or cod liver oil.

For subcutaneous or intravenous administration, the active compounds, if desired together with the substances which are customary for this purpose, such as solubilizers, emulsifiers or other auxiliaries, are dissolved, suspended or emulsified. Examples of suitable solvents are: water, physiological saline or alcohols, for example ethanol, propanol, glycerol, and also sugar solutions, such as glucose or mannitol solutions, or else a mixture of the various solvents which have been mentioned above.

Pharmaceutical formulations which are suitable for administration in the form of aerosols or sprays are, for example, solutions, suspensions or emulsions of the active substance of the formula I in a pharmaceutically acceptable solvent, such as, in particular, ethanol or water, or else in a mixture of such solvents.

If required, the formulation can also contain other pharmaceutical auxiliaries, such as surfactants, emulsifiers and stabilizers, and a propellent gas. The concentration of active substance in such a preparation is generally from about 0.1 to 10, in particular from about 0.3 to 3% by weight.

The dose of the active substance of the formula I to be administered and the frequency of administration will depend on the power and duration of action of the compounds used; in addition also on the nature and severity of the disease to be treated and on the sex, age, weight and individual responsiveness of the mammal to be treated.

On average, the daily dosage rate of a compound of the formula I in the case of a patient of approximately 75 kg will be at least 0.001 mg/kg, preferably 0.01 mg/kg, up to not more than 10 mg/kg, preferably 1 mg/kg, of body weight. If the disease is acute, such as immediately after suffering a cardiac infarction, even higher and, in particular, more frequent, doses may be required, for example up to 4 single doses per day. In particular, for intravenous administration, such as in the case of a patient who has suffered an infarction and is under intensive care, up to 200 mg per day may be required.

List of abbreviations:

| | |
|---|---|
| MeOH | methanol |
| DMF | N,N-dimethylformamide |
| NBS | N-bromosuccinimide |
| AIBN | α,α-azobis-isobutyronitrile |
| EI | electron impact |
| DCI | desorption chemical ionization |
| RT | room temperature |
| EA | ethyl acetate (EtOAc) |
| DIP | diisopropyl ether |
| MTB | methyl tert.-butyl ether |
| mp | melting point |
| HEP | n-heptane |
| DME | dimethoxyethane |
| FAB | fast atom bombardment |
| $CH_2Cl_2$ | dichloromethane |
| THF | tetrahydrofuran |
| eq | equivalent |

Experimental Part

General protocol for the preparation of benzoylguanidines (I) Variant A: from benzoic acid (II, L=OH)

0.01M of the benzoic acid derivative of the formula II is dissolved or suspended in 60 ml of anhydrous THF, and 1.78 g (0.011M) of carbonyldiimidazole are then added. The mixture is stirred for 2 hours at RT, and 2.95 g (0.05M) of guanidine are then introduced into the reaction solution. The mixture is stirred overnight, and the THF is then distilled off under reduced pressure (Rotavapor), water is added, the mixture is brought to pH 6 to 7 using 2N HCl, and the corresponding benzoylguanidine (formula I) is removed by filtration. The resulting benzoylguanidines can be converted into the corresponding salts by treating them with aqueous, methanolic or etheric hydrochloric acid or other pharmacologically acceptable acids.

General protocol for the preparation of benzoylguanidines (I) Variant B: from alkyl benzoates (II, L=O-alkyl)

5 mmol of the alkyl benzoate of the formula II and 25 mmol of guanidine (free base) are dissolved in 15 ml of isopropanol or suspended in 15 ml of THF, and the solutions, or suspensions, are refluxed until the reaction is complete (control by thin-layer chromatography; typical reaction time 2 to 5 hours). The solvent is distilled off under reduced pressure (Rotavapor), the residue is taken up in 300 ml of EE, and the mixture is washed 3× using in each case 50 ml of $NaHCO_3$ solution. The ethyl acetate phase is dried over $Na_2SO_4$, the solvent is distilled off in vacuo, and the residue is chromatographed on silica gel using a suitable solvent, for example EE./MeOH 5:1.

(Salt formation see Variant A)

EXAMPLE 1

4-(4-Pyridylthio)-3-methylsulfonylbenzoylguanidine

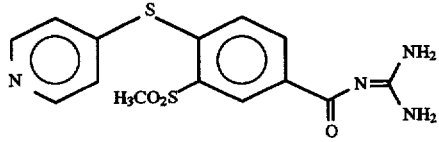

a) Methyl 4-(4-pyridylthio)-3-methylsulfonylbenzoate 6 mmol of methyl 4-chloro-3-methylsulfonylbenzoate, 18 mmol of $K_2CO_3$ and 6 mmol of 4-pyridylthiol are stirred in 30 ml of (anhydrous) DMF for 1 h at 130° C. The mixture is subsequently poured into 100 ml of saturated aqueous $NaHCO_3$ solution, and this is extracted 3× using 100 ml of EA. The ethyl acetate phase is dried over $Na_2SO_4$, the solvent is removed in vacuo, and the residue is chromatographed on silica gel using MTB. Pale yellow crystals, mp 112° C., $R_f$(MTB)=0.17
MS (DCl): 324 (M+1)

b) 4-(4-Pyridylthio)-3-methylsulfonylbenzoylguanidine 3.6 mmol of ester 1a) and 18.1 mmol of guanidine are reacted in accordance with general protocol B. White crystals, mp 205° C.

$R_f$(EE/MeOH 5:1)=0.24
MS (DCl): 351 (M+1)

EXAMPLE 2

4-(2-Pyridylthio)-3-methylsulfonylbenzoylguanidine

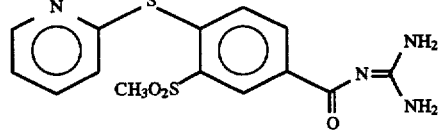

mp 207° C.
$R_f$(EA/MeOH 5:1)=0.27
MS (DCl): 351 (M+1)

EXAMPLE 3

4-(3-Pyridyloxy)-3-methylsulfonylbenzoylguanidine

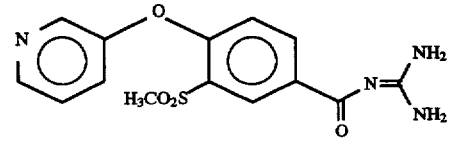

a) Methyl 4-(3-pyridyloxy)-3-methylsulfonylbenzoate 2 mmol of methyl 4-chloro-3-methylsulfonylbenzoate, 2 mmol of 3-pyridinol and 6 mmol of $K_2CO_3$ were stirred in 20 ml of (anhydrous) DMF for 2 h at 130° C. The mixture is subsequently poured into 100 ml of saturated aqueous $NaHCO_3$ solution and this is extracted 3× using 100 ml of EA. The ethyl acetate phase is dried over $Na_2SO_4$, the solvent is removed in vacuo, and the product is further reacted without further purification.

$R_f$(MTB)=0.15
MS (DCl): 308 (M+1)

b) 4-(3-Pyridyloxy)-3-methylsulfonylbenzoic acid 2 mmol of ester 3a) are dissolved in 20 ml of MeOH, and 5 equivalents of 2N aqueous NaOH are added. The solution is stirred for 3 h at RT, 50 ml of 0.3M aqueous KH$_2$PO$_4$ solution are added, and the mixture is extracted 3× using 50 ml of EA. The ethyl acetate phase is dried over Na$_2$SO$_4$ solution, the solvent is removed in vacuo, and the product is further reacted without further purification.

R$_f$ (EE/MeOH 5:1)=0.14
MS (DCI): 294 (M+1)

c) 4-(3-Pyridyloxy)-3-methoxysulfonylbenzoylguanidine 2 mmol of benzoic acid 3b), 2.2 mmol of carbonyldiimidazole and 10 mmol of guanidine are reacted in accordance with the general protocol A.

White crystals mp 202° C.
R$_f$ (EA/MeOH) 5:1)=0.38
MS (DCI): 335 (M+1)

The title compounds of Examples 4 to 10 are synthesized analogously to Example 3:

EXAMPLE 4

4-(2-Pyridyloxy)-3-methylsulfonylbenzoylguanidine

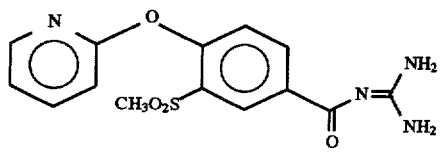

amorphous;
R$_f$ (EA/MeOH 5:1)=0.41
MS (DCI): 335 (M+1)

EXAMPLE 5

4-(4-Pyridyloxy)-3-methylsulfonylbenzoylguanidine

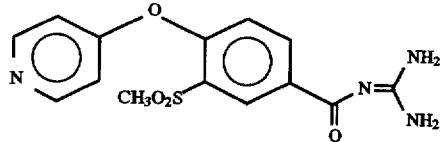

amorphous;
R$_f$ (EA/MeOH 3:1)=0.22
MS (DCI): 335 (M+1)

EXAMPLE 6

4-(7-Isoquinolinoxy)-3-methylsulfonylbenzoylguanidine

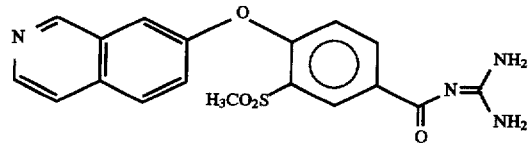

mp 103° to 105° C.
R$_f$ (EA/MeOH5:1)=0.23
MS (DCI): 385 (M+1)

EXAMPLE 7

4-(5-Isoquinolinoxy)-3-methylsulfonylbenzoylguanidine

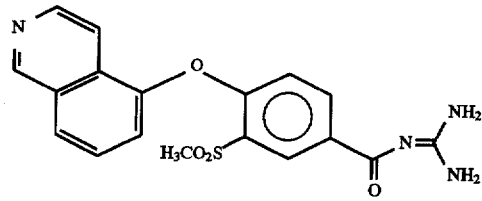

amorphous;
R$_f$ (EA/toluene/MeOH 3:3:1)=0.21
MS (DCI): 335 (M+1)

EXAMPLE 8

4-(5-Quinolinoxy)-3-methylsulfonylbenzoylguanidine

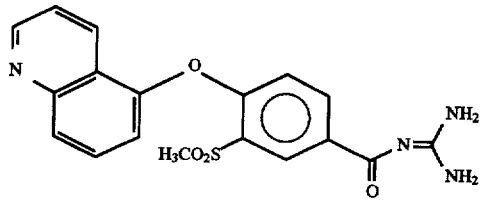

amorphous;
R$_f$ (EA/MeOH 5:1)=0.23
MS (DCI): 385 (M+1)

EXAMPLE 9

4-(6-Quinolinoxy)-3-methylsulfonylbenzoylguanidine

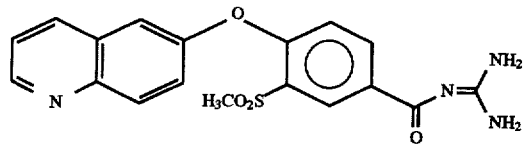

amorphous;
R$_f$ (EA/toluene/MeOH 3:3:1)=0.24
MS (DCI): 385 (M+1)

EXAMPLE 10

4-(8-Quinolinoxy)-3-methylsulfonylbenzoylguanidine

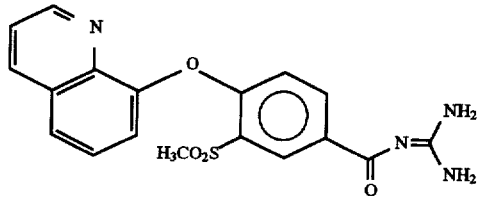

amorphous;
R$_f$ (EA/MeOH 5:1)=0.23
MS (DCI): 385 (M+1)

General protocol for the preparation of 4-(1-pyrrolo)-benzoic acids:

0.01 mol of a 4-aminobenzoic acid are dissolved in 20 ml of glacial acetic acid and 0.01 mol of 2,5-dimethoxytetrahydrofuran are then added. The mixture is stirred for 15 minutes at room temperature and for 1 hour while boiling. Then, the mixture is allowed to cool and is poured into 200 ml of water. The crystalline precipitate is filtered off and washed a few times with water, and the resulting 4-(1-pyrrolo)-benzoic acid is dried in the air.

The subsequent reaction of a 4-(1-pyrrolo)benzoic acid with guanidine after a preceding activation with carbonyldiimidazole gives, according to the general protocol A for the preparation of benzoylguanidines, the corresponding 4-(1-pyrrolo)benzoyl-guanidines and the salts thereof:

EXAMPLE 11

3,5-Dichloro-4-(1-pyrrolo)benzoylguanidine hydrochloride is prepared according to general Protocol A from 3,5-dichloro-4-(1-pyrrolo)benzoic acid, colorless crystals, m.p. 274° C.

3,5-Dichloro-4-(1-pyrrolo)benzoic acid (m.p. 178°–181° C.) is prepared from 3,5-chloro-4-aminobenzoic acid according to the general protocol for the preparation of 4-(1-pyrrolo)-benzoic acids.

EXAMPLE 12

3-Chloro-5-methyl-4-(1-pyrrolo)benzoylguanidine hydrochloride is prepared according to general protocol A from 3-chloro-5-methyl-4-(1-pyrrolo)benzoic acid, colorless crystals, m.p. 236°–238° C.

3-Chloro-5-methyl-4-(1-pyrrolo)benzoic acid (m.p. 160°–162° C., dec.) is prepared from 3-chloro-5-methyl-4-aminobenzoic acid according to the general protocol for the preparation of 4-(1-pyrrolo)-benzoic acids.

EXAMPLE 13

3,5-Dimethyl-4-(1-pyrrolo)benzoylguanidine hydrochloride is prepared according to general protocol A from 3,5-dimethyl-4-(1-pyrrolo)benzoic acid, colorless crystals, m.p. 261°–263° C.

3,5-Dimethyl-4-(1-pyrrolo)benzoic acid (m.p. 197°–200° C.) is obtained from 3,5-dimethyl-4-aminobenzoic acid according to the general protocol for the preparation of 4-(1-pyrrolo)-benzoic acids.

General protocol for the preparation of 4-[4-(1,2,4-triazolyl)]benzoic acids 0.01 mol of a methyl ester of a 4-aminobenzoic acid is suspended in 40 ml of boiling phosphorus oxychloride (POCl$_3$) while stirring. 0.044 mol of N,N'-diformylhydrazine are then added and this is then refluxed for 45 minutes. The excess POCl$_3$ is distilled off, and then the residue, which is mostly dark and viscous, is treated with 200 ml of a saturated aqueous sodium acetate. The precipitate is filtered off and washed several times with water.

0.01 mol of the resulting methyl 4-[4-(1,2,4-triazolyl)]benzoate is hydrolyzed for 6 hours using a boiling mixture of 18 ml of pure acetic acid and 36 ml of 20 per cent aqueous hydrochloric acid; thus, the corresponding 4-[4-(1,2,4-triazolyl)]benzoic acid is obtained.

The subsequent reaction of 4-[4-(1,2,4-triazolyl)]benzoic acid with guanidine after activation with carbonyldiimidazole according to the General protocol for the preparation of benzoylguanidines, gives the corresponding 4-[4-(1,2,4-triazolyl)]-benzoylguanidine or the salts thereof.

EXAMPLE 14

3,5-Dibromo-4-[4-(1,2,4-triazolyl)]benzoylguanidine dihydrochloride is obtained according general protocol A from 3,5-dibromo-4-[4-(1,2,4-triazolyl)]benzoic acid, colorless crystals, m.p. >290° C.

3,5-Dibromo-4-[4-(1,2,4-triazolyl)benzoic acid (m.p. 281°–282° C.) is obtained from methyl 3,5-dibromo-4-[4-(1,2,4-triazolyl)]benzoate (m.p.:202°–204° C.) according to the general protocol for the preparation of 4-[4-(1,2,4-triazolyl)]benzoic acids.

EXAMPLE 15

4-Imidazolyl-3-trifluoromethylbenzoylguanidine dihydrochloride: colorless crystals, m.p. 244°–48° C., dec.

Synthesis:

a) 4-fluoro-3-trifluoromethylbenzoylguanidine from 4-fluoro-3-trifluoromethylbenzoic acid and guanidine according to variant A, colorless powder, m.p. 136°–38° C.

b) 4-imidazolyl-3-trifluoromethylbenzoylguanidine dihydrochloride from a) by heating for 7 hours (120° C.) in DMF in the presence of 2 eq of imidazole, distilling off the solvent and treating the residue with water. Formation of the salt according to variant A.

EXAMPLE 16

4-(3-Pyridyloxy)-3-trifluoromethylbenzoylguanidine

a) Methyl 4-(3-pyridyloxy)-3-trifluoromethylbenzoate 2 mmol of methyl 4-fluoro-3-trifluoromethyl benzoate, 2 mmol of 3-hydroxypyridine and 4 mmol of K$_2$CO$_3$ are stirred for 1.5 hours at 110° C. in 15 ml of DMF (anhydrous). The mixture is subsequently poured into 100 ml of water and extracted 3× using in each case 50 ml of EA. The product is dried over Na$_2$SO$_4$, the solvent is removed in vacuo, and the product is reacted further without further purification. 500 mg of colorless oil.

R$_f$(MTB)=0.33

MS (EI): 298 (M+1)

b) 4-(3-Pyridyloxy)-3-trifluoromethylbenzoylguanidine 1.7 mmol of methyl 4-(3-pyridyloxy)-3-trifluoromethylbenzoate are converted to the acylquanidine following Variant B (reaction time 2 hours). 300 g of an amorphous solid are obtained.

R$_f$(EA/MeOH 10:1)=0.18 m.p. (dihydrochloride)=245° C.

MS (EI): 325 (M+1)

The title compound of Example 17 is synthesized analogously to Example 16:

EXAMPLE 17

4-(6-Quinolinoxy)-3-trifluoromethylbenzoylguanidine

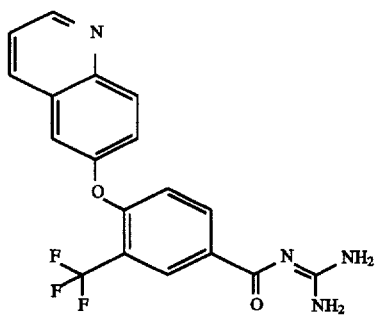

$R_f$(EA/MeOH 10:1)=0.17 m.p. (dihydrochloride)=115° C. (decomposition)

MS (EI): 375 (M+1)

Pharmacological data:

Inhibition of the $Na^+/H^+$ exchanger of rabbit erythrocytes

White New Zealand rabbits (Ivanovas) were given a standard diet containing 2% of cholesterol for six weeks so as to activate the $Na^+/H^+$ exchange in order to be able to determine the $Na^+$ influx into the erythrocytes via $Na^+/H^+$ exchange by means of flame photometry. The blood was sampled from the auricular artery and made incoagulable by addition of 25 IE of potassium heparin. Part of each sample was used for a repeated hematocrit measurement by centrifuging. 100 µl aliquots were used for measuring the initial $Na^+$ content of the erythrocytes.

To determine the amiloride-sensitive sodium influx, 100 µl of each blood sample were incubated in in each case 5 ml of a hyperosmolaric salt/sucrose medium (mmol/l: 140 NaCl, 3 KCl, 150 sucrose, 0.1 ouabain, 20 tris-hydroxymethylaminomethane) at pH 7.4 and 37° C. Then, the erythrocytes were washed three times using ice-cold $MgCl_2$/ouabain solution (mmol/l: 112 $MgCl_2$, 0.1 ouabain) and hemolyzed in 2.0 ml of distilled water. The intracellular sodium content was determined by flame photometry.

The $Na^+$ net influx was calculated from the difference between the initial sodium values and the sodium content of the erythrocytes after incubation. The sodium influx which can be inhibited by amiloride was determined from the difference of the sodium content of the erythrocytes after incubation with and without amiloride $3\times10^{-4}$ mol/l. The same procedure was used for the compounds according to the invention.

Results
Inhibition of the $Na^+/H^+$ exchanger:

| Example | $IC_{50}$ µmol/l |
|---|---|
| 16 | 0.03 |
| 17 | 0.04 |

We claim:
1. A benzoylguanidine of the formula I

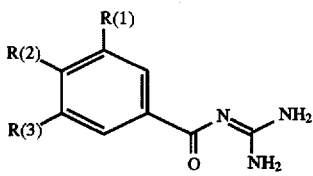

R(1) is hydrogen, F, Cl, Br, I, $-NO_2$, $-C\equiv N$, R(16)—$C_pH_{2p}-O_q$, R(4)—$SO_m$ or R(5)R(6)N—$SO_2$—;
is zero, 1, 2 or 3;
q is zero or 1;
R(16) is $C_rF_{2r+1}$;
r is 1, 2 or 3,
m is zero, 1 or 2;
R(4) and R(5) independently of one another are $(C_1-C_8)$-alkyl, $(C_3-C_6)$-alkenyl, $-C_nH_{2n}$—R(7) or CF3;
n is zero, 1, 2, 3 or 4
R(7) is $(C_3-C_7)$-cycloalkyl or phenyl, which is unsubstituted or substituted by 1-3 substituents selected from the group consisting of F, Cl, $CF_3$, methyl, methoxy and NR(8)R(9);
R(8) and R(9) independently of one another are H or $C_1-C_4$-alkyl; or
R(5) is H;
R(6) H or $(C_1-C_4)$-alkyl; or
R(5) and R(6) are together 4 or 5 methylene groups, of which one $CH_2$ group can be replaced by oxygen, S, NH, N—$CH_3$ or N-benzyl;
R(2) is $(C_1-C_9)$-heteroaryl, which is linked via C or N and which is unsubstituted or substituted by 1-3 substituents selected from the group consisting of F, Cl, $CF_3$, $CH_3$, methoxy, hydroxy, amino, methylamino and dimethylamino; or
R(2) is —SR(10), —OR(10), —NR(10)R(11) or —CR(10)R(11)R(12);
R(10) is —$C_aH_{2a}$—$(C_1-C_9)$-heteroaryl, which is unsubstituted or substituted by 1-3 substituents selected from the group consisting of F, Cl, $CF_3$, $CH_3$, methoxy, hydroxyl, amino, methylamino and dimethylamino;
a is zero, 1 or 2;
R(11) and R(12) independently of one another have the definition given R(10) or are hydrogen or $(C_1-C_4)$-alkyl;
R(3) has the definition given for R(1) or is $(C_1-C_6)$-alkyl or —X—R(13);
X is oxygen, S or NR(14);
R(14) is H or $(C_1-C_3)$-alkyl;
R(13) is H, $(C_1-C_6)$-alkyl, $(C_3-C_8)$-cycloalkyl:or —$C_bH_{2b}$—R(15);
b is zero, 1, 2, 3 or 4;
R(15) is phenyl which is unsubstituted or substituted by 1-3 substituents selected from the group consisting of F, Cl, $CF_3$, methyl, methoxy and NR(8)R(9);
R(8) and R(9) independently of one another are H or $(C_1-C_4)$-alkyl;
with the exception of compounds I in which R(1) is R(4)-$SO_m$ or R(5)$NSO_2$ and R(2) simultaneously is $(C_1-C_9)$-heteroaryl,
and the pharmaceutically acceptable salts thereof.
2. A compound of the formula I as claimed in claim 1, in which R(1) is hydrogen, F, Cl, —C≡N, R(16)—$C_pH_{2p}$—$O_q$, R(4)—$SO_m$ or R(5)R(6)N—$SO_2$—;
p is zero, 1, 2 or 3;
q is zero or 1;
R(16) is $C_rF_{2r+1}$;
r is 1, 2 or 3;
m is zero, 1 or 2;
R(4) and R(5) independently of one another are ($C_1$–$C_8$)-alkyl, ($C_3$–$C_4$)-alkenyl, —$C_nH_{2n}$—R(7) or —$CF_3$;
n is zero or 1;
R(7) is ($C_3$–$C_6$)-cycloalkyl or phenyl, which is unsubstituted or substituted by 1–3 substituents selected from the group consisting of F, Cl, $CF_3$, methyl, methoxy and NR(8)R(9);
R(8) and R(9) independently of one another H or methyl; or
R(5) is H;
R(6) is H or methyl;
R(3) is hydrogen, methyl, cyano, —$CF_3$, F or Cl,
and the remaining radicals are as defined in claim 1.

3. A compound of the formula I as claimed in claim 1, in which

R(1) is hydrogen, F, Cl, —C≡N, —$CF_3$, R(4)—$SO_m$ or R(5)R(6)N—$S_2$;
m is zero, 1 or 2;
R(4) is methyl or CF3;
R(5) and R(6) independently of one another are H or methyl;
R(2) is ($C_1$–$C_9$)-heteroaryl, which is linked via C or N and which is unsubstituted or substituted by a radical selected from the group consisting of F, Cl, $CF_3$, $CH_3$, methoxy and dimethylamino; or
R(2) is —SR(10), —OR(10), —NR(10) R(11) or —CR(10) R(11) R(12);
R(10) is —$C_aH_{2a}$—($C_1$–$C_9$)-heteroaryl, which is unsubstituted or substituted by a radical selected from the series consisting of F, Cl, $CF_3$, $CH_3$, methoxy and dimethylamino;
a is zero, 1 or 2;
R(11) and R(12) independently of one another are hydrogen or methyl;
R(3) is methyl, cyano, trifluoromethyl, F, Cl or hydrogen.

4. A process for the preparation of a compound I as claimed in claim 1, which comprises reacting a compound of the formula II

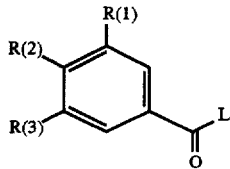

in which R(1) to R(3) are as defined in claim 1 and L is a leaving group which can readily be substituted by a nucleophile, with guanidine.

5. A method of making a pharmaceutical composition for the treatment of cardiac arrhythmias comprising adding an effective amount of a compound of formula I of claim 1 to a pharmaceutically acceptable carrier.

6. A method of making a cardioprotective pharmaceutical composition for the prophylaxis and treatment of infarctions and of angina pectoris comprising adding an effective amount of a compound of formula I of claim 1 to a pharmaceutically acceptable carrier.

7. A pharmaceutical composition for the treatment of cardiac arrhythmias, infarcation, and for cardioprotection, which comprises an effective amount of a compound of formula I of claim 1 and at least one suitable additive.

8. A method of treating arrhythmias, infarctions, and for cardioprotection, which comprises administering an effective amount of a "compound" of formula I of claim 1, which has been additioned with the customary additives and brought into a suitable dosage form.

9. A method of treating prophylaxis of ischemic heart conditions comprising administering to a host suffering from prophylaxis a compound of the formula I of claim 1.

10. The benzoylguanidine of claim 1 wherein R(1) is hydrogen, R(2) is 3-pyridyloxy and R(3) is a trifluoromethyl radical.

11. The benzoylguanidine of claim 1 wherein R(1) is hydrogen, R(2) is 6-quinolinoxy and R(3) is a trifluromethyl radical.

* * * * *